(12) United States Patent
Hebert

(10) Patent No.: US 6,630,511 B2
(45) Date of Patent: Oct. 7, 2003

(54) WATER-SOLUBLE SALTS OF 2-DIFLUOROMETHYL-2,5-DIAMINOPENTANOIC ACID (DFMO)

(76) Inventor: Rolland F. Hebert, 427 Bellevue Ave. E #301, Seattle, WA (US) 98102

( * ) Notice: Subject to any disclaimer, the term of this patent is extended or adjusted under 35 U.S.C. 154(b) by 0 days.

(21) Appl. No.: 09/919,692

(22) Filed: Jul. 31, 2001

(65) Prior Publication Data

US 2002/0019338 A1 Feb. 14, 2002

Related U.S. Application Data

(60) Provisional application No. 60/222,420, filed on Aug. 1, 2000.

(51) Int. Cl.7 .............................................. A61K 31/195
(52) U.S. Cl. ...................................................... 514/561
(58) Field of Search .......................................... 514/561

(56) References Cited

U.S. PATENT DOCUMENTS

| | | | | |
|---|---|---|---|---|
| 4,413,141 A | * | 11/1983 | Bey | |
| 4,499,072 A | * | 2/1985 | Sunkara et al. | |
| 4,720,489 A | * | 1/1988 | Shander | |

OTHER PUBLICATIONS

Proc Natl Acad Sci USA 1982; 79:6028–32.*

* cited by examiner

Primary Examiner—Rebecca Cook

(57) ABSTRACT

Water-soluble salts of 2-difluoromethyl-2,5-diaminopentanoic acid (DFMO) with polycations, their synthesis and uses are described.

2 Claims, No Drawings

WATER-SOLUBLE SALTS OF 2-DIFLUOROMETHYL-2,5-DIAMINOPENTANOIC ACID (DFMO)

CROSS-REFERENCES TO RELATED APPLICATION

This application claims the benefit of Provisional Patent Application Ser. No. 60/222,420 filed on Aug. 1, 2000.

BACKGROUND

1. Field of the Invention

The present invention relates to new salts of 2-difluoromethyl-2,5-diaminopentanoic acid (DFMO).

2. Technical Field

This patent relates to new salts of 2-difluoromethyl-2,5-diaminopentanoic acid (DFMO) with polycations such as polycationic carbohydrates (chitosan, water-soluble chitosan derivative, or a salt thereof) or a polyaminoacid, a polyamine, a polypeptide, a basic polymer, a quartinary ammonium compound or a mixture thereof, the processes for obtaining them and to therapeutic uses of these new salts. DFMO, in vitro and in vivo, is an inhibitor of ornithine decarboxylase, an enzyme that is involved in polyamine formation in organisms.

BACKGROUND OF THE INVENTION

In both eukaryotic and prokaryotic cells, the decarboxylation of ornithine to putrescine, a reaction catalyzed by ornithine decarboxylase (ODC), is the first step in the biosynthesis of the polyamines known as spermidine and spermine. The polyamines, which are found in animal tissues and microorganisms, are known to play an important role in cell growth and proliferation. The onset of cell growth and proliferation is associated with a marked increase in ODC activity and an increase in the levels of putrescine and the polyamines. Although the exact mechanism of the role of the polyamines in cell growth and proliferation is not known, it appears that the polyamines may facilitate macromolecular processes such as DNA, RNA, or protein synthesis. (Tabor H, Tabor C W, Cohn M S, Hafner E W. Streptomycin resistance produces an absolute requirement for polyamines for growth on an *Escherichia coli* strain unable to synthesize spermidine. J Bacteriolol 1981; 147: 702–4; Mamont P S, Bohelen, P, McCann P P, Bey P, Schuber R, Tardif C. Alpha-methyl ornithine, a potent competitive inhibitor of ornithine decarboxylase, blocks proliferation of rat hepatoma cells in culture. Proc Natl Acad Sci USA 1976; 73: 1626–30.)

The association between high levels of the polyamines and rapid proliferation was discovered more than a quarter of a century ago. (Bachrach U and Weinstein A. Effect of aliphatic polyamines on growth and macromolecular syntheses in bacteria. J. Gen. Microbiol., 60: 159–165 1970.) Subsequent studies showed that activation of the enzyme ODC was important for carcinogenesis and subsequent tumor development in animal and tumor models. (Weeks C E, Hrrmann A L, Nelson F R, Slaga T J. Alpha difluoromethylornithine, an irreversible inhibitor of ornithine decarboxylase, inhibits tumor promoter-induced polyamine accumulation and carcinogenesis in mouse skin. Proc Natl Acad Sci USA 1982; 79:6028–32.)

It is currently known that increased intracellular polyamine concentrations are related to human neoplastic conditions. (Verma, A K Inhibition of tumor promotion by DL-alphadifluoromethylornithine, specific irreversible inhibitor of ornithine decarboxylase. Basic Life Sci., 52:195–204, 1990). A further example of this relationship between high polyamine concentrations and neoplasms involves colonic polyps and cancers compared to surrounding normal colon mucosa. (Hixson, L J, Garewal, H S, McGee D., Sloan D, Fennerty, M B, Sampliner R E and Gemer E W. Omithine decarboxylase and polyamines in colorectal neoplasia and adjacent mucosa. Cancer Epidemiol. Biomark. Prev. 2;369–374, 1993; Rozhin J, Wilson P S, Bull A W, and Nigro, N D. Ornithine decarboxylase activity in the rat and human colon. Cancer Res. 44: 3226–3230, 1984.)

Other groups have reported that polyamine metabolism was necessary for carcinogenesis, especially in epithelial tissues. ODC inhibitors have been found to inhibit or suppress tumor formation in models of bladder, breast, colon and skin carcinogenesis. (Verma, A K Inhibition of tumor promotion by DL-alpha-difluoromethylornithine, specific irreversible inhibitor of ornithine decarboxylase. Basic Life Sci., 52:195–204, 1990; Nigro N D, Bull A W and Boyd, M E. Inhibition of intestinal carcinogenesis in rats: effect of difluoromethylornithine for colon cancer prevention. J. Natl Cancer Inst. 77: 1309–1313, 1986; Thompson H J, and Ronan Am. Effect of DL-2-difluoromethylornithine and endocrine manipulation on the induction of mammary carcinogenesis by 1-methyl-1-nitrosourea. Carcinogenesis (Lond.), 7: 20032006, 1986.)

It is thought, however, that the mechanism of cancer prevention by ODC inhibitors such as DFMO may involve more than just inhibition of cell proliferation. Animal studies show that DFMO may act at later stages in models of chemical carcinogenesis. These stages involve the transition of non-invasive tumors to invasive cancers. (Slaga, T J. Multistage skin carcinogenesis: a useful model for the study of the chemoprevention of cancer. Acta Pharmacol. Toxicol., 55 (Suppl. 2): 107–124, 1984.)

DFMO has been studied and continues to be studied as a cancer prevention agent, especially in skin, cervical and colon cancer. (Love R R, Carbone, P P Verma, A K, Gilmore D, Carey P, Tutsch K D. Pomplun M, and Wilding G. Randomized Phase I chemoprevention dose-seeking study of alpha-difluoromethylornithine. J. Natl. Cancer Inst., 85:732–736, 1993; Nishioka K, Melgarejo A B, Lyon R R and Mitchell M F. Polyamines as biomarkers of cervical intraepithelial neoplasia. J. Cell. Biochem., 23 (Suppl.): 87–95, 1995; Mitchell M F, Tortolero-Luna G, Lee J J, Hittelman W N, Lotan R, Wharton J T, Hong, W K and Nishioka, K. Phase I dose de-escalation trial of alpha-difluoromethylornithine in patients with grade 3 cervical intraepithelial neoplasia. Clin. Cancer Res., 4:303–310, 1998; Meyskens F I, Emerson S S, Pelot D, Meshkinpour H, Shassetz R, Einspahr J, Alberts D S, and Gerner, E W. Dose de-escalation chemoprevention trial of alpha-difluoromethylornithine in patients with colon polyps. J. Natl. Cancer Inst., 86:1122–1130, 1994.)

While high doses of DFMO in humans can cause some problems with hearing (reversible upon discontinuation of DFMO), at the doses used for chemoprevention of cancer (0.50 g/m2/day) such concerns have been found to be groundless. (Meyskens F L, Gerner E, Emerson S, Pelot D, Durbin T, Doyle K and Lagerber W. A randomized double-blind placebo controlled Phase IIb trial of difluoromethylornithine for colon cancer prevention. J. Natl. Cancer Inst., 90: 1212–1218, 1998).

DFMO has also been found useful in conditions unrelated to cancer. ODC inhibitors have been associated with control of hair growth. Studies in mice have suggested that the ODC gene is an important regulatory gene for the mouse hair follicle. (Soler A P, Gilliard G, Megosh L C, O'Brien T G.J Modulation of murine hair follicle function by alterations in ornithine decarboxylase activity. Invest Dermatol 1996 May;106(5):1108–13.) The FDA, to control facial hair growth in women, has recently approved DFMO. (Current DFMO salts, when used topically, cause burning, irritation and inflammation.) DFMO may have use in controlling male facial hair growth as well and may constitute a methodology to supplant or reduce the use of razors to remove facial hair in men. New DFMO salts, which are the subject of this invention, have been shown to be less irritating, do not cause burning and inflammation when applied topically.

REVIEW OF PRIOR ART

U.S. Pat. No. 4,330,559, May 18, 1982, Bey, et al. discloses the use of DFMO to treat benign prostatic hypertrophy. U.S. Pat. No. 4,399,151, Aug. 16, 1983, Sjoerdsma, et al. discloses the use of 2-(difluoromethyl)-2,5-diaminopentanoic acid (DFMO) for inhibiting the growth of protozoa. U.S. Pat. No. 4,405,530, Sep. 20, 1983, Gerhart, discloses the preparation of fluorinated amino-nitriles. These patents do not disclose the preparation or use of new DFMO salts of the present invention made with chitosan or polycations.

U.S. Pat. No. 4,413,141, Nov. 1, 1983 Bey, et al. discloses 2-(difluoromethyl)2,5-diaminopentanoic acid (DFMO) and the methods for the preparation and use thereof U.S. Pat. No. 4,499,072, Feb. 12, 1985, Sunkara, et al. discloses the use of DFMO as an ODC inhibitor along with interferon in treating diseases. U.S. Pat. No. 4,720,489, Jan. 19, 1988, Shander, discloses the use of DFMO as an ornithine decarboxylase inhibitor to modify hair growth. These patents do not disclose the preparation and use of new DFMO salts of the present invention made with chitosan or polycations.

U.S. Pat. No. 5,648,394 Jul. 15, 1997, Boxall, et al. discloses the use of DFMO as a topical composition for inhibiting hair growth but does not teach the use of new DFMO salts of the present invention made with chitosan or polycations. WO9814188, 1998-04-09, Love et al. teaches the use of preparations comprising a single enantiomer or defined ratio of enantiomers of alphadifluoromethylornithine (DFMO) for treating, preventing, controlling the growth of and/or reducing the risk of developing estrogen independent breast cancer or tumor and for administering DFMO alone or in combination with taxol. However, this patent does not teach the preparation and use of new DFMO salts of the present invention made with chitosan or polycations. U.S. Pat. No. 5,851,537, Dec. 22, 1998, Alberts et al. discloses the use of topical application of DFMO to prevent skin cancer but does not teach the preparation and use of new DFMO salts of the present invention made with chitosan or polycations. WO0069434, 2000-11-23, Love discloses the use of Celecoxib, a COX-2 specific non-steroidal anti-inflammatory agent, in combination with DFMO for the prevention and/or treatment of cancers. However, this patent does not teach the preparation and use of new DFMO salts of the present invention made with chitosan or polycations. U.S. Pat. No. 6,166,079, Dec. 26, 2000, Follen et al. discloses the use of DFMO for the treatment or prevention of cervical intraepithelial neoplasia. U.S. Pat. No. 6,258,845, Jul. 10, 2001, Gemer, et al. discloses the use of DFMO and sulindac combination in cancer chemoprevention. These patents do not teach the preparation and use of new DFMO salts of the present invention made with chitosan or polycations.

Administration of agents that inhibit ornithine decarboxylase would have significant utility over a wide range of disorders or conditions associated with an increase polyamine metabolism. For example, in addition to the prevention and/or treatment of different types of cancer or pre-cancer conditions, such agents would have utility in preventing and/or treating colon polyps, benign prostatic hypertrophy (BPH), or hirsutism. Such agents may also provide a means to decrease the need for daily shaving of facial hair in males.

Accordingly, there is a need in the art for agents that inhibit ODC, as well as methods related to the use of such agents to prevent and/or treat conditions associated with increased polyamine metabolism. There is also a need in the art for synthetic routes to make such agents. The present invention fulfills these needs, and provides further related advantages.

SUMMARY OF THE INVENTION

Briefly stated, the present invention discloses new DFMO salts, methods for the use thereof and synthetic methods for their preparation. These new salts of DFMO of this present invention have utility in treating or preventing a variety of conditions related to the aforementioned mechanisms of action of DFMO, namely ODC inhibition. Thus in one embodiment, a new DFMO salt is administered to a warm-blooded animal in need thereof. In yet a further embodiment, a new DFMO salt is administered to a warm blooded animal to prevent and or treat the following conditions: aging of the skin, cancer, HIV, alopecia, solar keratosis, benign prostatic hypertrophy, prostate cancer, breast cancer, cervical cancer, and other such conditions in which polyamine metabolism requires modulation. Such a salt may be administered along with any other agent to enhance its therapeutic effectiveness. Other aspects of the present invention will become evident upon reference to the following detailed description.

DETAILED DESCRIPTION OF THE INVENTION

As mentioned above, this invention is generally directed to new water-soluble salts of DFMO. Such new DFMO salts, when administered to a warm-blooded animal in need thereof, have utility in the prevention or treatment of conditions enumerated above in warm-blooded animals, including humans.

The term "treat" or "treatment" means that the symptoms associated with one or more conditions mentioned above are alleviated or reduced in severity or frequency and the term "prevent" means that subsequent occurrences of such symptoms are avoided or that the frequency between such occurrences is prolonged.

It has now surprisingly been found that salts of DFMO with chitosan, a polycation, have good characteristics that are such as to render them particularly suitable both for use in pharmaceutical formulations and for preparative applications.

Owing to their simple conception and low costs, the procedures described in this invention easily lend themselves to working out methods of preparation on an industrial scale.

The examples given herein below illustrate the preparation of two salts of DFMO with chitosan (as only one example of a polycation according to this invention). Only a few of the many possible embodiments that may be anticipated are shown by these examples which are intended to define, in a non-limiting sense, the scope encompassed by the invention. The examples illustrate two possible synthetic routes according to the invention as well as the complete absence of side effects when a 20% cream is applied topically to the forearm of healthy volunteers.

These examples are given to illustrate the present invention, but not by way of limitation. Accordingly, the scope of this invention should be determined not by the embodiments illustrated, but rather by the appended claims and their legal equivalents.

EXAMPLE 1

DFMO (0.21 g) was stirred in water (20 ml) and chitosan (0.10 g, degree of deacetylation 80.1%) was added with stirring. The solution was stirred until dissolved. The solution was filtered and dried.

EXAMPLE 2

DFMO (0.21 g) was stirred in water (20 ml) and chitosan (0.20 g, degree of deacetylation 80.1%) was added with stirring. The solution was stirred until dissolved. The solution was filtered and dried.

DFMO and chitosan are available commercially from Sigma Chemical Company, St. Louis, Mo.

EXAMPLE 3

A 20% cream made of this new salt of DFMO was applied to the forearm of 10 healthy individuals twice daily for a two-week period in an outpatient clinic. No patients complained of burning, irritation, scaling or redness after the cream. Patients returned to the clinic after having used the cream for two weeks for a visual inspection of the forearm area. The examining physician noted no redness, irritation or scaling in the area where the cream had been applied.

I claim:

1. A composition comprising a salt of alpha.difluoromethylornithine (DFMO) and chitosan.

2. A method of preparing the salt of alpha.difluoromethylornithine and chitosan which comprises stirring alpha.difluoromethylornithine and chitosan in water until dissolved into solution and then filtering and drying the solution.

* * * * *